(12) United States Patent
Riley

(10) Patent No.: US 7,527,428 B2
(45) Date of Patent: May 5, 2009

(54) PLATFORM FOR RADIOLOGICAL EXAMINATION OF THE FOOT AND ANKLE

(76) Inventor: Thomas J. Riley, 811 Bromfield Terr., Manchester, MO (US) 63021

( * ) Notice: Subject to any disclaimer, the term of this patent is extended or adjusted under 35 U.S.C. 154(b) by 0 days.

(21) Appl. No.: 11/681,415

(22) Filed: Mar. 2, 2007

(65) Prior Publication Data

US 2008/0209636 A1 Sep. 4, 2008

(51) Int. Cl.
*G03B 42/02* (2006.01)
(52) U.S. Cl. .............................. 378/177; 378/208; 5/601
(58) Field of Classification Search ................. 378/167, 378/192, 204, 205, 208, 177; 5/601, 624
See application file for complete search history.

(56) References Cited

U.S. PATENT DOCUMENTS 5,920,606 A * 7/1999 Sohr ........................... 378/177

* cited by examiner

*Primary Examiner*—Jurie Yun
(74) *Attorney, Agent, or Firm*—Charles McCloskey

(57) ABSTRACT

A two step platform elevates a standing patient upon a horizontally located chamber for examination of the foot and ankle by radiological methods. The chamber receives a slide that carries an x-ray film beneath a foot of a standing patient. Additionally, the patient stands upon a visually and radiologicaly transparent deck. The deck has one slot for upright positioning and a chamber for horizontal positioning of a radiological film cartridge. The platform of the present invention allows a radiologist to take a radiological image of a patient's foot and ankle from both the side and above.

5 Claims, 8 Drawing Sheets

PLATFORM FOR RADIOLOGICAL EXAMINATION OF THE FOOT AND ANKLE

BACKGROUND OF THE INVENTION

The platform for radiological examination of the foot and ankle generally relates to medical furniture and more specifically to a platform that positions a radiological plate below or adjacent to a foot.

In medical offices and x-ray rooms across the country, numerous radiological examinations, hereinafter x-rays, are taken of patients and their conditions. Conditions include wounds and injuries to the foot. To determine the extent of a wound or injury, or the progress of healing, x-rays are taken of a foot. X-ray equipment can be positioned at various angles to shoot a beam through the subject part of the body and into a plate. The plate is then developed and the resulting x-ray film is provided to a doctor for evaluation. X-rays can be taken of a patient's foot and ankle as the patient sits and the equipment is positioned near the foot. However, such x-ray films show a foot or ankle without bearing a load, or weight. Those x-ray films show the bony structure in the absence of stress thus limiting the appearance of cracks in the bony structure.

As feet and ankles move and support a person's weight throughout the day and during exertion, x-rays of feet and ankles when under stress provide a more accurate view of the condition of the feet and ankles. Feet and ankles x-rayed while under stress may reveal cracks in the bony structure closed when the feet and ankles are not stressed. Operators of x-ray equipment and doctors have sought devices to assist in x-raying feet and ankles while supporting weight.

DESCRIPTION OF THE PRIOR ART

Over the years, feet and ankles have been x-rayed with the support of various devices. Initially, feet and ankles were merely positioned between an x-ray source and a plate containing x-ray film, usually with the patient seated upon a chair or upon a bench. This method did not provide x-rays of feet and ankles when supporting weight. Operators then placed the plate containing the film upon a floor and the patient stood with a foot upon the plate. As the plate has a thickness, the posture of the patient went out of alignment and the x-ray of the foot showed bony structure also out of position. Operators then had a patient stand upon an elevated platform, such as books or boxes, and suspend the foot and ankle above the plate. As before, this method showed a foot and ankle on the x-ray film that was not supporting weight and with posture out of line.

The prior art has developed various stands. Clear Image Devices of Ann Arbor Michigan has a two step positioning platform for timely and accurate x-rays of the lower extremities. This platform has an upper step with three spaced apart grooves extending longitudinally. The upper step is opaque to visible light but presumably transparent to x-ray and other radiation. The slots allow upright positioning of the x-ray plate and the two step design raises the foot to the height of the x-ray emitter. As the x-ray plate is positioned upright, the platform does not provide a location for the plate to capture an image of the foot from above when the foot supports a person's weight. This platform appears directed primarily to x-rays of the ankle to the exclusion of the remainder of the foot.

The present invention overcomes the difficulty of x-raying the foot from above when bearing weight.

SUMMARY OF THE INVENTION

Generally, the present invention provides a two step platform with a horizontally located chamber. The chamber receives a slide that carries an x-ray film beneath a foot of a standing patient. Additionally, the patient stands upon a visual light and x-ray transparent deck. The deck has one slot for upright positioning of an x-ray film cartridge and a chamber for horizontal positioning of an x-ray film cartridge. The platform of the present invention allows a radiologist to take an x-ray image of a patient's foot and ankle from both the side and from above.

There has thus been outlined, rather broadly, the more important features of the invention in order that the detailed description thereof that follows may be better understood and that the present contribution to the art may be better appreciated. The present invention also includes a slide for carrying the x-ray film cartridge into and out of the chamber, casters upon the rear for easing movement of the invention when it is up ended, and front and rear feet for raising the platform above a floor surface. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the present invention is to provide a new and improved platform for radiological examination of the foot and the ankle of a person.

Another object is to provide such a platform that positions a radiological film cartridge below a person's weight bearing foot for examination from above.

Another object is to provide such a platform that allows a person to see the radiological cartridge below the person's foot during examination.

Another object is to provide such a platform that inserts and removes a radiological film cartridge from within a chamber across the width of said platform.

Another object is to provide such a platform that moves easily when raised upright onto its rear.

Another object is to provide such a platform that occupies a minimum of floor space when raised upon end.

Another object is to provide such a platform that resists racking and distortion both widthwise and lengthwise.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
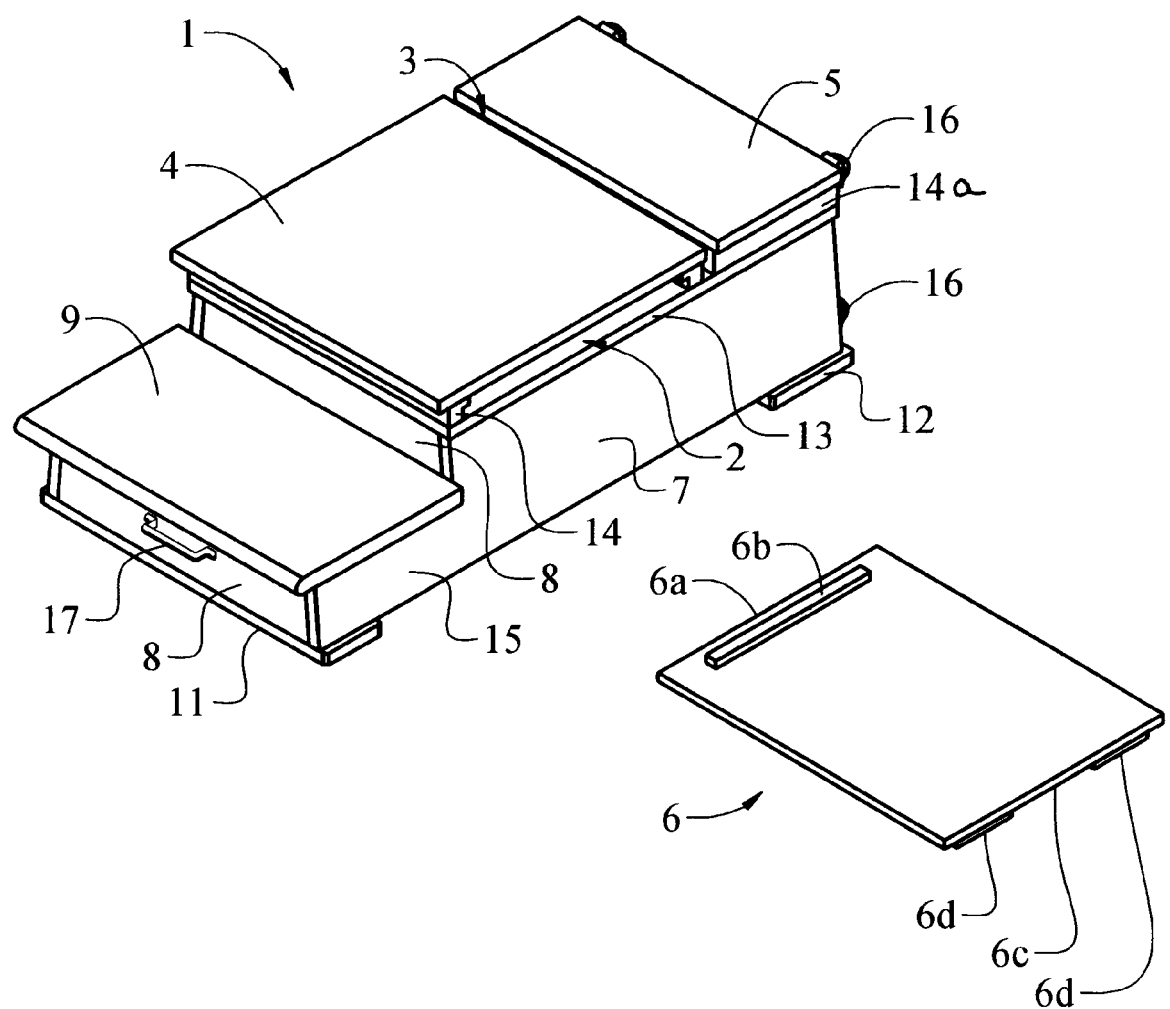
FIG. 1 shows an isometric view of the present invention ready for use with its appurtenant slide.

The present invention of the platform overcomes the prior art limitations by providing a platform 1 that has a chamber 2 and a nearby slot 3 for placing radiological film cartridges, hereinafter x-ray film, for usage in taking images of a person's ankle or foot while bearing the weight of a person as shown in FIG. 1. The chamber is located beneath a transparent front deck 4 generally rectangular in shape and preferably square. The front deck is spaced apart from the rear deck 5 by the slot 3. The rear deck is also transparent and rectangular in shape with the same width as the front deck. The front deck and the rear deck are generally coplanar so that a person, or patient, may stand with one foot upon each deck and the foot for examination upon the front deck 4. The front deck and the rear deck are supported upon spacers 14 that elevate them from the remaining framework of the platform. The front deck and the rear deck are raised upon spacers 14 so that the chamber has sufficient height to admit an x-ray film when carried upon a slide 6 and the slot has sufficient depth to support an upright x-ray film respectively. The slot 3 has sufficient width to hold an x-ray film securely but permits medical staff to remove an exposed film.

The framework of the platform includes a plate 13, two inwardly angled sides 7, a kickplate 8 in two parts upon the front, a step 9, a base 10 upon the rear, a front foot 11, and a rear foot 12. The plate 13 is located below the front deck 4 and the rear deck 5 generally parallel to and spaced apart from the front deck. The spacers 14 upon the plate raise the front deck to create the chamber 2 for admitting an x-ray film upon the slide 6. The plate has longitudinal sides and lateral ends. The front deck extends slightly beyond the front lateral end of the plate. Two spaced apart sides 7 extend downwardly from the plate and flare outwardly. The sides are planar and substantially rectangular in shape. The sides have an extension 15 forward of the front deck 4 that serves as a riser for step 9. The extension is generally half the width of the remainder of a side. Ahead of the front deck and between the sides 7, the framework has two kickplates, one kickplate 8 located beneath the step 9 and between the extensions 15 has a handle 17, and a second kickplate 8 located immediately beneath the front deck between the sides where each extension joins the remainder of a side.

Then a step connects to the first kickplate at the end of the extensions and extends rearward upon the interior edge of the extension until it contacts the remainder of the sides. The step has a width slightly larger than the width of the front deck. The front of the step, or nose, is rounded over for the ease and comfort of patients during usage of the invention. Opposite the kickplates 8 and near the intersection of the rear deck 5 and the sides 7, the framework has a base 10 that connects the plate to the sides and supports casters 16 as later shown in FIG. 4. Below the rear deck where the base connects with the sides at their widest point, the framework has the rear foot 12. The rear foot spans the sides with generally the same width as the rear deck. The rear foot has a length less than that of the rear deck. Forward of the rear foot, the framework has a front foot 11 located below the step where the first kickplate connects to the sides. The front foot has a length much less than the step and a width proximate to that of the step. The front foot, rear foot, kickplates, base, sides, and plate cooperate to form a generally trapezoidal shaped framework that supports the front and rear decks when a patient climbs upon the present invention in the position shown in FIG. 1.

Two spaced apart sides connect the plate, base, rear foot, front foot, kickplates, and step. The sides are mirror images so only one will be described. A side has a generally rectangular shape that spans in height from the plate to the rear foot and in length from the base to the inside edge of the step and the kickplate above the step. The side has an extension 15 forward that passes under the step and connects to the front foot. The extension also has a rectangular shape coplanar with the remainder of the side. The extension has a length slightly less than the depth of the step and a height similar to that of the lower kickplate, generally proportional to a stair riser in height. The side is tilted at an inward angle so the framework attains a generally trapezoidal shape when viewed on end.

The present invention also includes a slide 6 that carries an x-ray into the chamber 2. The slide has a generally rectangular form with a length slightly greater than the length of the chamber and a width similar to that of the chamber. The slide has a forward edge 6a that enters the chamber and a stop 6b proximate the forward edge. The stop has less width than the slide and retains the x-ray film upon the slide when the slide is pulled out of the chamber. As later shown in FIG. 2, the slide has a rearward edge 6c with at least one grip 6d located below the slide, generally opposite the stop.

Figure 2:
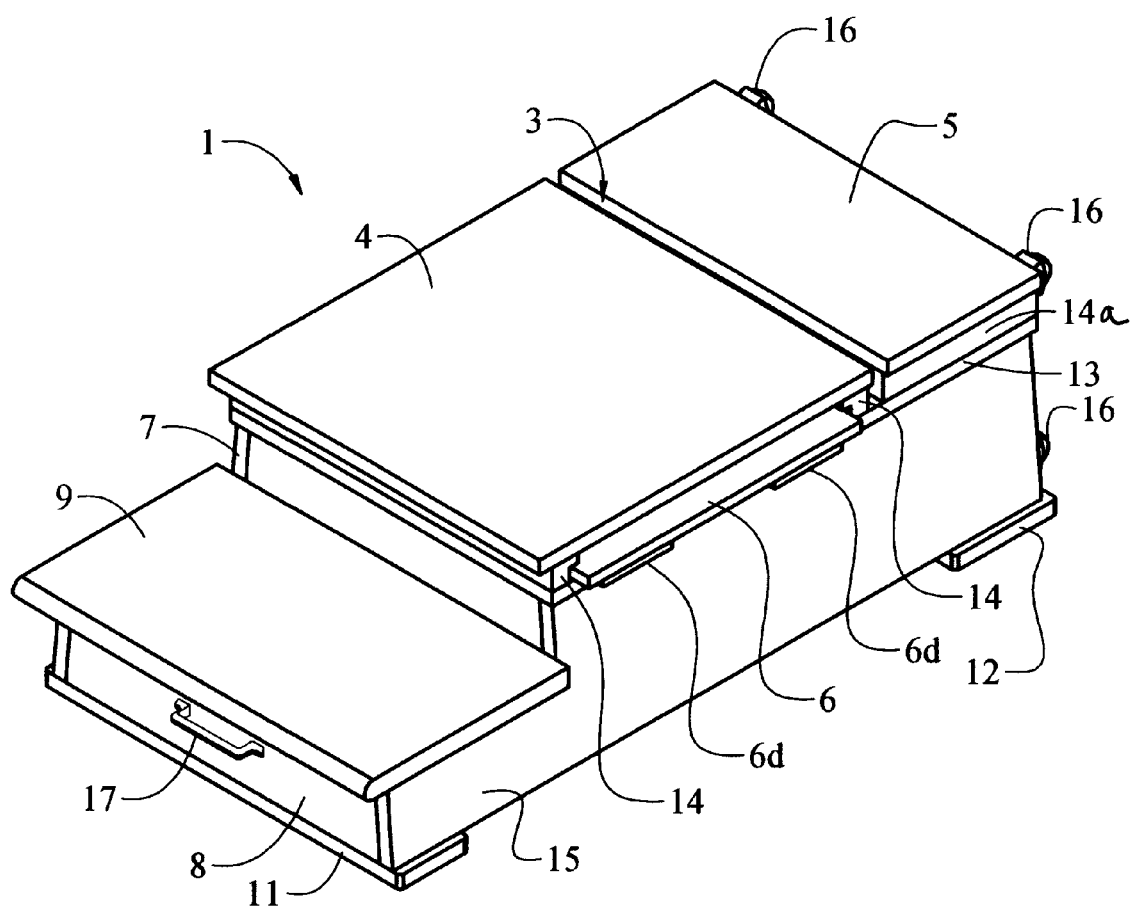
FIG. 2 shows another isometric view of the present invention with the slide placed within the chamber.

The present invention is shown ready for a patient to have a foot x-rayed upon the front deck in FIG. 2. As before, the platform has a framework of members that support the front deck and the rear deck with a slot between the two decks. Here, the front deck 4 connects to spacers 14 laterally near the front of the plate 13 and the slot 3. The spacers in raising the front deck above the plate establish a chamber 2 that receives the slide 6 as in FIG. 2. The slide has a rearward edge 6c shown outward of the side in this view with grips 6d shown below the slide proximate the edge of the plate. The grips prevent the slide from fully entering the chamber and assists in proper positioning of x-ray film within the chamber during usage.

Figure 3:
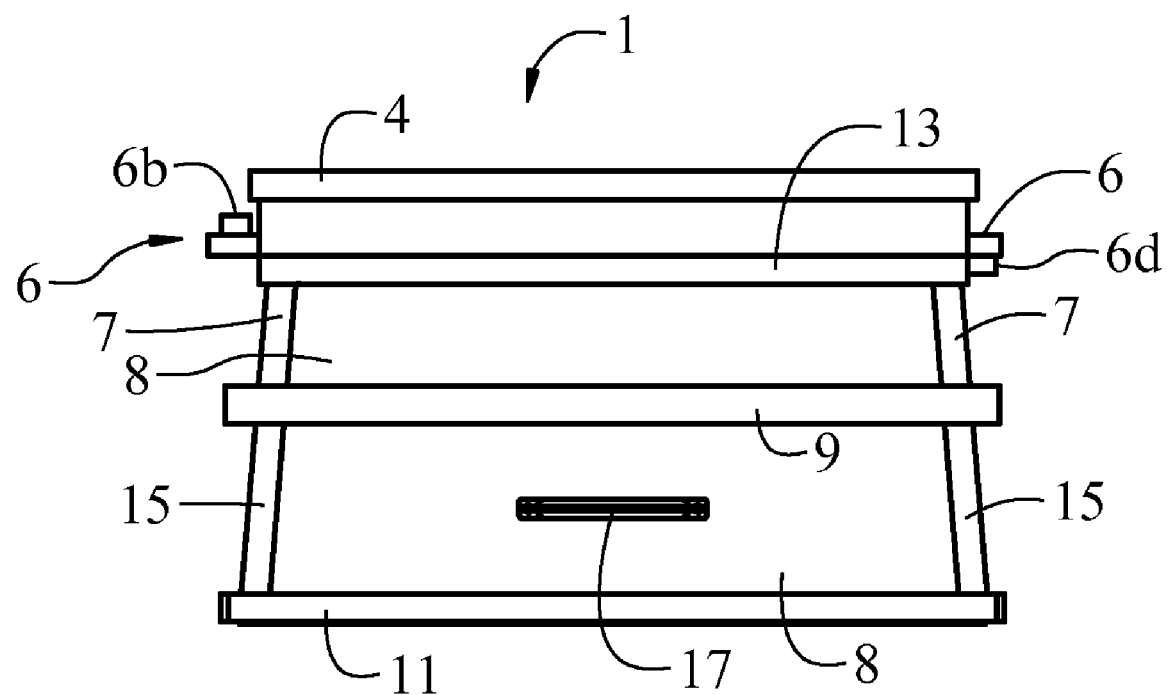
FIG. 3 describes a front view of the present invention.

The platform is shown from the front in FIG. 3 as a patient would access the invention during usage. The platform has a front foot 11 spanning the width of the invention and a kickplate 8 extending upwardly from the front foot. In an alternate embodiment, the kickplate has a handle 17 generally centered thereon to assist a person in lifting the platform upward for movement and storage as later described. Outwardly of the kickplate, the front has the extensions 15 of the sides 7 that connect the kickplate to the front foot and support the step 9. The step is connected to the extensions and the kickplate generally parallel to the front foot. The step spans across the width of the platform at generally one half of the total height of the platform. The step has a rounded edge towards the front for the comfort of the patients who access the platform generally barefoot.

Behind the step, the sides 7 extend upwardly and have a second kickplate 8 spanning between them. At the top of the sides and the kickplate, the plate 13 connects to the sides. The plate is generally parallel to the step and the front foot. The plate extends rearward for the length of the side without extension. The plate has a spacer 14 extending perpendicular and upward from the front edge that raises the front deck 4 to its operational height, the full height of the invention. The front deck is generally planar and horizontal when in use as shown in this figure. The front deck, plate, step, and front foot are mutually parallel and spaced apart. Behind the spacer, the slide 6 is shown inserted with the forward edge to the left and the stop 6b extending upwardly. The upward stop retains the x-ray film upon the slide when the slide is removed from the chamber 2. The slide shows the rearward edge to the right and the grips 6d extending below the slide 6. The grips below abut the plate 13 and prevent the slide for slipping further into the chamber or falling out of the chamber while carrying an x-ray film during usage.

Figure 4:
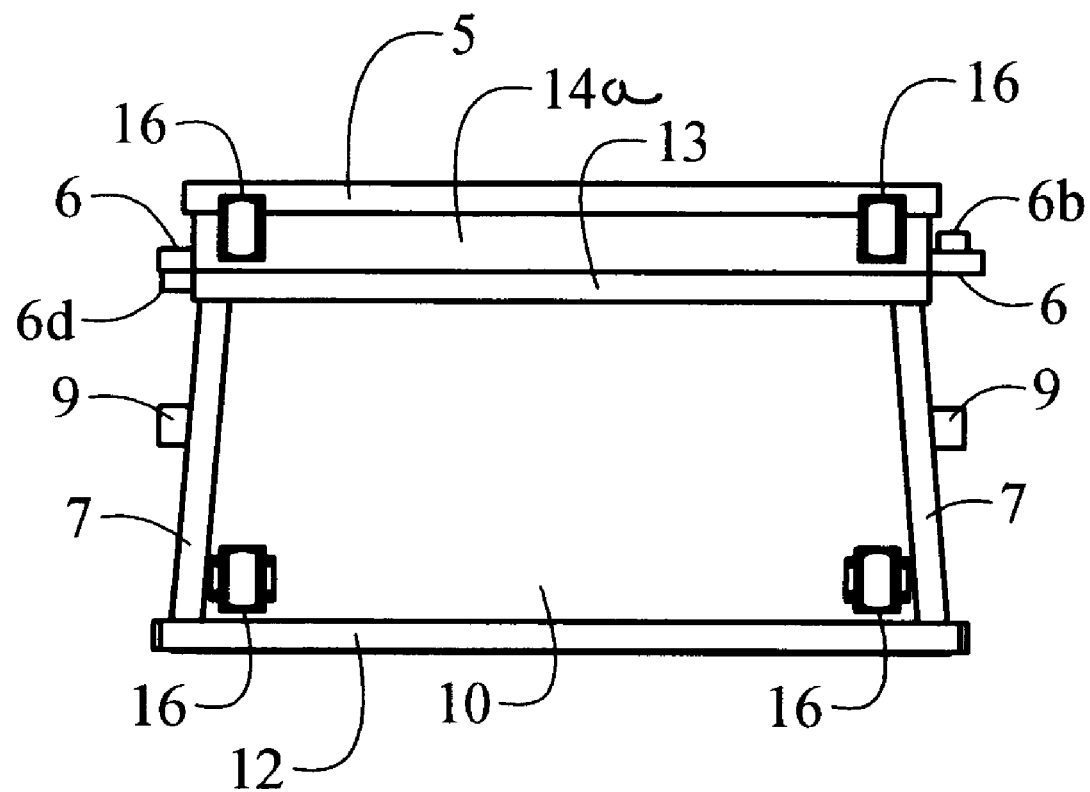
FIG. 4 describes a rear view of the present invention.

Rotating the invention, FIG. 4 shows the rear of the invention where a rear foot 12 has a similar width to the front foot that establishes the width of the invention. The sides 7 extend upwardly from the rear foot towards the full height of the invention. The sides angle inwardly to form a trapezoidal shape with the plate 13 at the top. The plate spans across the invention from side to side. Within the sides, rear foot, and plate, the rear has a base 10. The base connects to the adjoining members and in cooperation with the kickplates and step in the front provides stiffness, or rigidity, to the invention when bearing the weight of a patient. Behind the base, the step 9 is shown in the background with portions extending outwardly from the sides 7. As in the front, the rear has a spacer 14a connected to the plate at the end near the base. The spacer extends for the width of the plate and raises the rear deck 5 above the plate to the same elevation as the front deck. The spacer 14a beneath the rear deck is shown wider than the spacer 14 for the front deck because the rear deck lacks a chamber beneath it. In an alternate embodiment, the platform includes a second, narrower chamber beneath the rear deck and similarly sized second slide. As before, the slide 6 extends through the chamber as shown in the foreground. The stop 6b is shown to the right and the grip is shown to the left. The platform has at least three casters 16 installed near the base with four shown here. The casters are of swiveling, Simpson type and rotate into the direction of movement for the platform. Here, two casters mount to the corners of the base with the rear foot and two casters mount upon the flush ends of the rear deck and the spacer.

Figure 5:
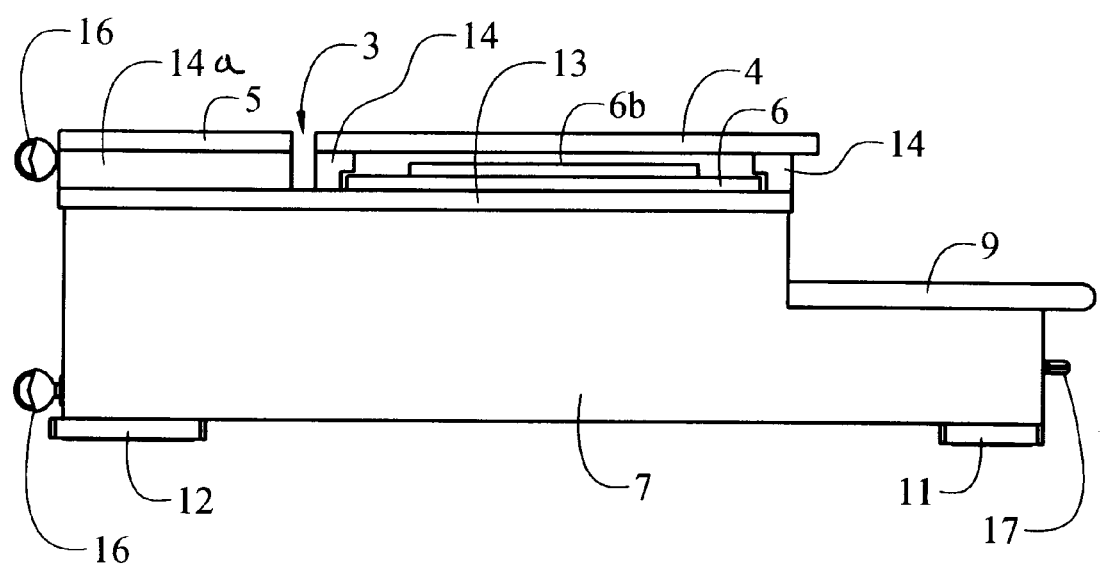
FIG. 5 shows a side view of the platform with the slide resting in the chamber.

FIG. 5 shows a side view of the platform 1 with the forward edge 6a and stop 6b of the slide shown. The side 7 has a generally rectangular form with an extension 15 upon one lateral end. The extension supports the step 9 that attaches to the length of the extension upon the inside angle of the extension and the remainder of the side. The front foot 11 attaches beneath the extension at the outside corner. Opposite the front foot, the rear foot 12 attaches to the side at the other outside corner below the elevation of the step. Above the front foot, rear foot, and the step, the plate attaches to the top of the sides generally parallel to the step. Upon the plate, the spacers 14 attach, mutually parallel and spaced apart to form the slot and then the chamber. The spacer adjacent to the base and away from the step is the same width as the rear deck above. The spacer near the base ends at the slot 3 that itself has a width to admit an x-ray film. The chamber 2 is formed between two spacers 14 of generally inverted L shape cross section, mutually parallel and spaced apart to admit the slide 6. Upon the spacer 14a near the base, the rear deck 5 attaches and the front deck 4 attaches to the two spaced apart spacers 14 above the chamber 2. Upon the base, spacer, and plate, the casters attach and generally have their axes of rotation parallel to the plane of the base.

Figure 6:
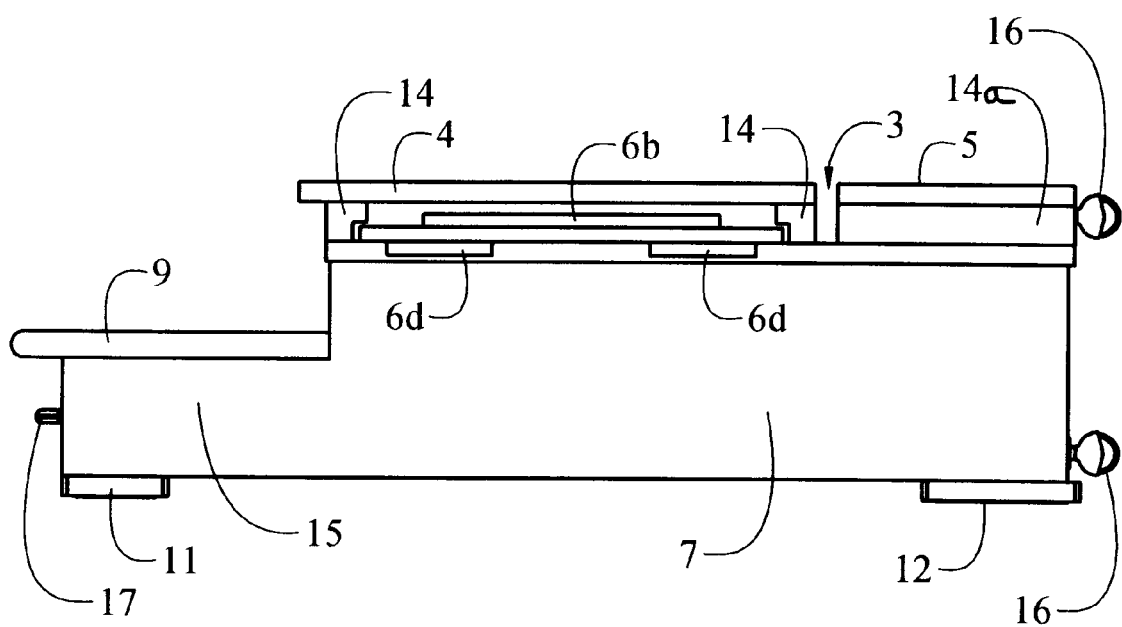
FIG. 6 shows the other side view of the platform with the slide inserted into the chamber from this side.

FIG. 6 shows the opposite side view of FIG. 5. The sides, front foot, and rear foot and related framework are symmetric to that described above. In this view, the slide 6 is shown inserted into the chamber 2. In the background the slide has the stop 6b shown within the outline of the chamber. In the foreground the slide 6 has the rearward edge 6c shown with the grips 6d below. The stop extends for substantially the width of the slide and is generally a narrow elongated cross section. The grip is generally shown in two separated pieces that allow for grasping of the slide from either the front or the rear by an x-ray operator.

Figure 7:
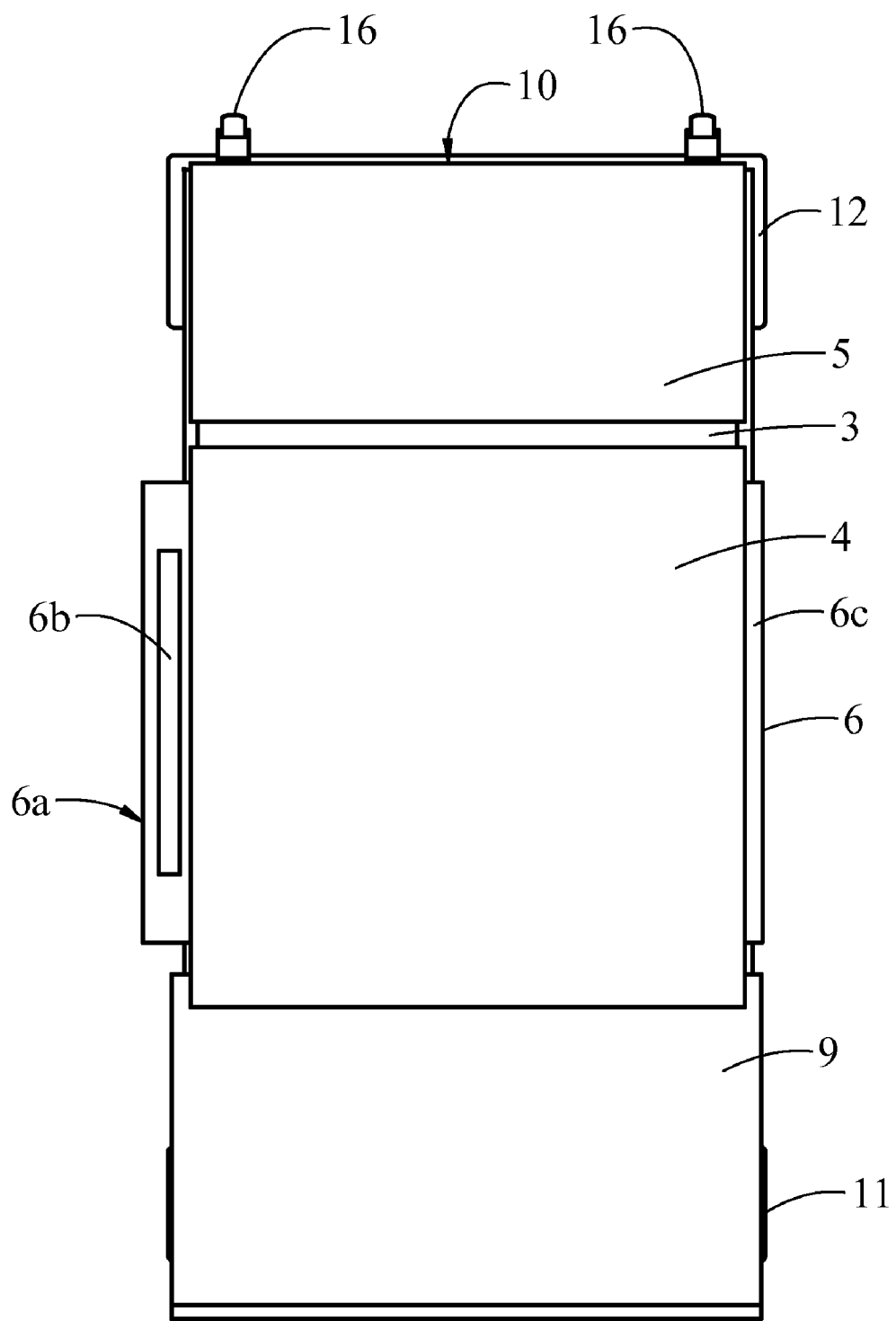
FIG. 7 illustrates a top view of the platform.
Figure 8:
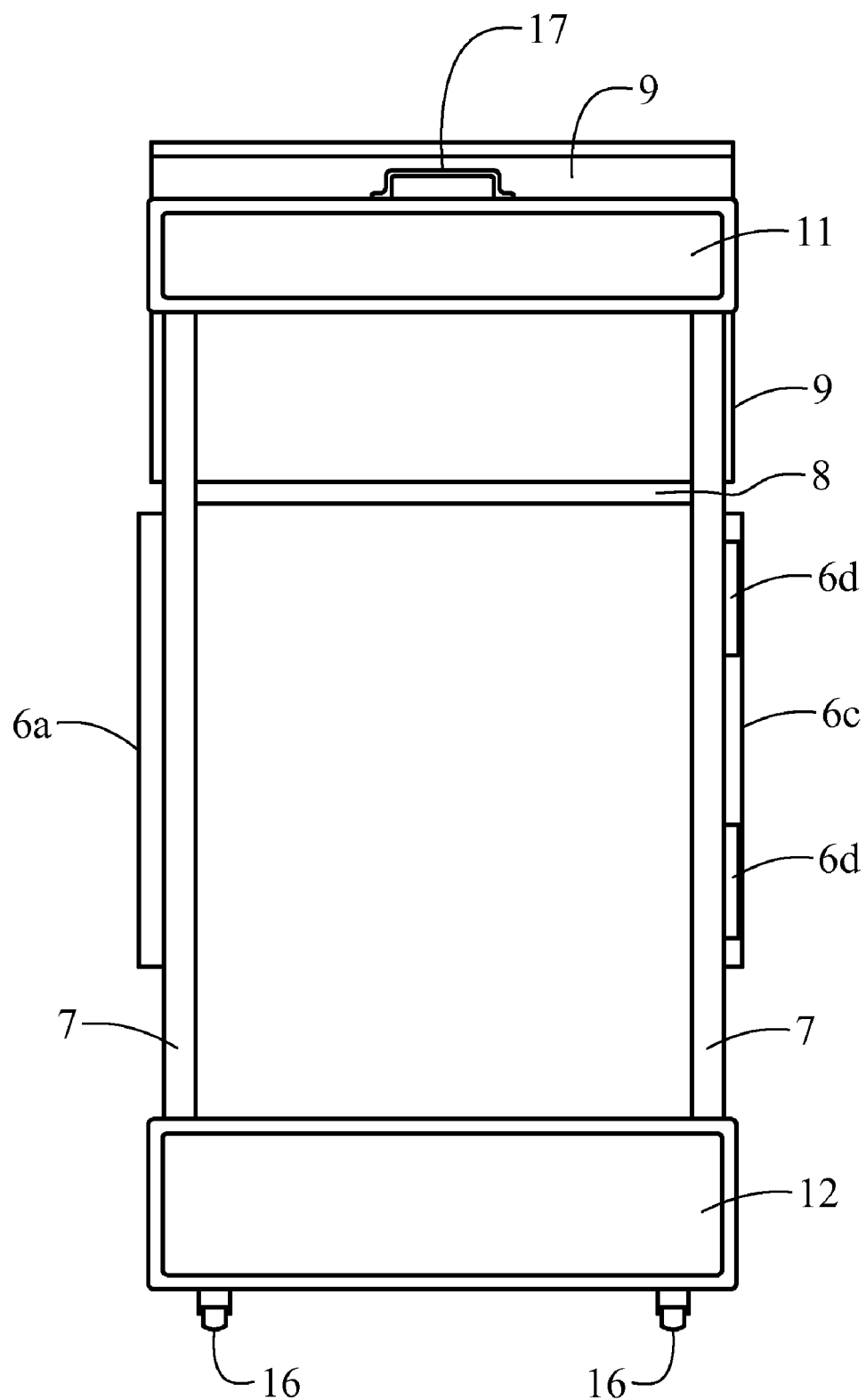
FIG. 8 illustrates a bottom view of the platform of this invention.

The platform appears from above in FIG. 7 as seen by the patient, or the x-ray emitter above. A patient enters the platform from the front at the step 9. Above the step, the sides support the plate and then the front deck 4. The front deck is located rearward of the step and has a chamber below it for the x-ray film. The x-ray film is inserted and removed from the chamber using the slide 6. Here, the slide is inserted into the chamber with the stop 6b shown to the left. The stop extends substantially across the width of the slide to hold an x-ray film placed thereupon. Behind the front deck, the platform has a slot 3 that receives an x-ray film located upon edge. Behind the slot, the platform comes to an end with the rear deck 5. The rear deck and front deck are coplanar and at the same elevation above the step. And, FIG. 8 shows a bottom view of the platform 1 and a view of the platform when lifted upright upon the casters for movement. The platform has a framework assembled from the spaced apart sides 7, the laterally extending kickplates 8 locating above the front foot 11 and the step 9, the base 10 at the rear or bottom of the invention, and the rear foot 12 under the base. The front foot and the rear foot are generally perpendicular to the sides and located below the sides. The front foot and the rear foot are generally rectangular in shape with the rear foot being wider than the front foot. A handle upon the front kickplate 8 assists in lifting the invention and in steering it when in motion. Above the handle in this view, the step 9 extends outwardly across the width of the platform. Opposite the step, the platform has casters 16 upon the base and adjacent members that allow for movement of the platform. Between the front foot and the rear foot, this view shows the slide 6 inserted into the chamber 2. The slide has the grip 6d upon the left of the figure.

In the preferred embodiment as described above, the framework, its component members, and the slide are made from plywood and joined with carpentry joints and methods. Preferably, the component members are assembled using adhesives reinforced with screws and blocks.

From the aforementioned description, a platform for radiological examination of the foot and ankle has been described. The platform is uniquely capable of supporting a patient while standing upon a deck with an x-ray film beneath. The platform also supports the x-ray film on edge for side views of the foot and ankle while bearing weight. The platform is predominantly made from wood with a front deck made from Plexiglas to permit transmission of x-rays and light therethrough. The platform and its various components may be manufactured from many materials, including but not limited to, polymers, polyvinyl chloride, high density polyethylene, polypropylene, nylon, steel, ferrous and non-ferrous metals, their alloys, and composites.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

I claim:

1. A device for positioning a patient proximate radiological film for examination of a foot or an ankle of said patient while standing upon said device, comprising:

a platform having at least one fixed step, a radiologically and optically transparent front deck parallel to and above said step and a coplanar rear deck, a framework supporting said step and said front deck and said rear deck, a chamber transverse said platform. below and parallel to said front deck adapted to receive radiological film, and a slot between said front deck and said rear deck adapted to receive radiological film upon edge;

a slide adapted to carry radiological film into said chamber transversely, having a generally planar shape, forward edge, a mutually parallel and spaced apart rearward edge, at least one stop above said forward edge, and at least one grip below said rearward edge;

said at least one stop retaining the radiological film upon said slide and preventing said slide from passing through said chamber;

said at least one grip abutting said framework outside of said chamber;

said framework including a plate generally parallel to said front deck and said rear deck, at least two spacers locating between said plate and said front deck and establishing said chamber; and, said spacers having an inverted L shape defining said chamber wherein said chamber admits said forward edge and said stop.

2. A device for positioning a patient proximate radiological film for examination of a foot or an ankle of said patient while standing upon said device, comprising:

a platform having at least one fixed step, a radiologically and optically transparent front deck parallel to and above said step and a coplanar rear deck, a framework supporting said step and said front deck and said rear deck, a chamber transverse said platform, below and parallel to said front deck adapted to receive radiological film, and a slot between said front deck and said rear deck adapted to receive radiological film upon edge;

said framework having two spaced apart sides, each of said sides having a generally planar rectangular shape below said deck and an extension of lesser width denoting the front of said side, said sides tilting longitudinally inward, said fixed step located upon said extensions generally parallel to said deck, at least two kickplates locating between said extensions and said sides proximate the front, a plate generally parallel to said front deck and said rear deck, at least two spacers locating between said plate and said front deck establishing said chamber, a base locating between said sides opposite said extensions, and at least one foot locating below said sides.

3. The foot positioning device of claim 2 further comprising:

said rear deck being spaced apart from said front deck, wherein a patient having two feet places one foot of said patient upon said rear deck and the other foot of said patient upon said front deck for providing an image of only the other foot of said patient upon radiological film.

4. The foot positioning device of claim 3 further comprising:

said rear deck locating upon at least two other spacers, said other spacers exceeding the width of said spacers beneath said front deck, said other spacers connecting to said plate.

5. The foot positioning device of claim 2 further comprising:

at least three casters locating opposite said step and proximate said base wherein said casters allow for upright positioning and upright movement of said device with said base downwardly.

* * * * *